(12) United States Patent
Choi et al.

(10) Patent No.: US 6,277,643 B1
(45) Date of Patent: Aug. 21, 2001

(54) METHOD FOR DETECTION OF PROTEIN ON POLYACRYLAMIDE GELS USING A COUNTER-DYE COMPOSITION AND COUNTER-DYE COMPOSITION FOR THE SAME

(75) Inventors: Jung Kap Choi, Mirabo Apt. #305-807, Woonam-dong, Buk-ku, Kwangju 500-170; Gyoung Hoon Tak, 598-12, Dooam-2-dong, Buk-ku, Kwangju 500-102; Da-Woon Jung, Woosanjukong Apt. #105-906, Moonheung-dong, Buk-ku, Kwangju 500-110; Gyurng Soo Yoo, Hyundai Apt. #203-1204, Yongbong-dong, Buk-ku, Kwangju 500-070, all of (KR)

(73) Assignees: Jung Kap Choi; Gyoung Hoon Tak; Da-Woon Jung; Gyurng Soo Yoo, all of Kwangju (KR)

( * ) Notice: Subject to any disclaimer, the term of this patent is extended or adjusted under 35 U.S.C. 154(b) by 0 days.

(21) Appl. No.: 09/351,119

(22) Filed: Jul. 10, 1999

Related U.S. Application Data

(63) Continuation of application No. PCT/KR99/00105, filed on Mar. 4, 1999.

(30) Foreign Application Priority Data

Jul. 20, 1998 (KR) .................................................. 98-29104
Jan. 20, 1999 (KR) .................................................... 99-1672

(51) Int. Cl.[7] .............................. C09B 67/00; G01N 33/00
(52) U.S. Cl. ............................... 436/86; 436/88; 436/164; 436/166; 436/169; 436/174; 8/636; 8/657; 8/658
(58) Field of Search .............................. 436/86, 88, 164, 436/166, 169, 174, 179; 8/636, 657, 658

(56) References Cited

U.S. PATENT DOCUMENTS 4,966,854   10/1990   Fleming .
5,705,649   1/1998    Shultz et al. .

OTHER PUBLICATIONS

Choi, et al. A Modified Coomassie Blue Staining of Proteins in Polyacrylamide Gels with Bismark Brown R, Anal. Biochem. 236(1):82–4 (Apr. 5, 1996).*

* cited by examiner

*Primary Examiner*—Jill Warden
(74) *Attorney, Agent, or Firm*—Peter F. Corless; Dike, Bronstein, Roberts & Cushman, LLP

(57) ABSTRACT

The present invention relates to a method for detection of protein using a counter-dye composition, on polyaciylamide gels, and the counter-dye composition for detection of protein on polyacrylamide gels. More specifically, the present invention relates to a method for detection of protein in a high sensitivity on polyacrylamide gels in a rapid and simple manner, comprising the step of staining the polyacrylamide gels with a counter-dye composition containing an acidic organic dye and a basic organic dye, and the counter-dye composition for detection of protein on polyacrylamide gels.

6 Claims, 8 Drawing Sheets

↑ 25ng

↑ 1ng

↑ 1ng

↑ 25ng

↑25ng

↑50ng

METHOD FOR DETECTION OF PROTEIN ON POLYACRYLAMIDE GELS USING A COUNTER-DYE COMPOSITION AND COUNTER-DYE COMPOSITION FOR THE SAME

This Application is a continuation of PCT/KR99/00105 filed Mar. 4, 1999.

TECHNICAL FIELD

The present invention relates to a method for detection of protein on polyacrylamide gels using a counter-dye composition and the counter-dye composition for detection of protein on polyacrylamide gels. More specifically, the present invention relates to a method for detection of protein in a high sensitivity on polyacrylamide gels in a rapid and simple manner, comprising the step of staining polyacrylamide gels with a counter-dye composition containing an acidic organic dye and a basic organic dye, and the counter-dye composition for detection of protein on polyacrylamide gels.

BACKGROUND ART

Polyacrylamide gel electrophoresis (PAGE) is a protein analysis technique which is useful in the separation, identification, approval of purity and determination of size of protein. Particularly, SDS-PAGE (Sodium Dodesyl Sulfate-PAGE) is a method characterized in that protein binds intimately with an anionic surfactant, i. e. SDS, with the ratio of 1.4 to 1, so as to have (–) charge on the surface thereof, and thereby only the size thereof acts as a separation factor. This method is widely used in protein analysis because it can be simply-handled and has a good resolution (see [A.T. Andrews, Electrophoresis, 2nd Ed., Oxford Science Publications, 1–58, (1988)])

Since most of proteins, which are subjected to analysis, are colorless, an appropriate method must be considered for detection. Various detection methods have been reported to the present time such as organic dye staining method, silver staining method, fluorescence staining method and background staining method, etc.

Organic dye staining method is performed by staining protein band with an organic dye such as Amido black 10B, Ponceaus S, Fast green FCF, Coomassie brilliant blue R (abbreviated to CBBR), etc (see [J. of Chromatography A, 698, 123–143 (1995)]). Particularly, since CBBR staining method is relatively simple and inexpensive, it has been generally used. However, it has problems in requiring a long time staining and destaining procedure and not having so good sensitivity. (50 ng on Bovine serum albumin (BSA)).

Silver staining method is performed by adsorbing silver to gels and then, carrying out reduction reaction, which has the highest sensitivity among non-isotopic detection methods. Although its sensitivity reaches to 0.1 ng, it has problems in involving difficult and multiple steps.

Fluorescence staining method is performed by labelling protein with a fluorescent dye. Although it has high detection sensitivity, it has drawbacks in that it involves very complicated steps, and requires the radiation of ultraviolet rays and the use of expensive equipment for quantitation.

Background staining method is performed by forming precipitate on gels except for protein band, the use of which is limited to SDS gels. Although this method is rapid and useful, the resulting band is not persistent and it has difficulty in storing the stained gel. (see [Anal. Biochem. 174, 157–167 (1988)])

Under the above-described situation, it has been required to develop a novel method for detection of protein in a higher sensitivity than the prior method on polyacrylamide gels in a rapid and simple manner.

DISCLOSURE OF THE INVENTION

Accordingly, the purpose of the present invention is to provide a method which can solve the problems involved in the above-mentioned prior methods. Thus, the present invention relates to a method for detecting protein in a high sensitivity, and in a rapid and simple manner, by staining polyacrylamide gels with a counter-dye composition.

One aspect of the present invention provides a method for detection of protein on polyaciylamide gels comprising the step of staining the polyaciylamide gels with a counter-dye composition containing an acidic organic dye and a basic organic dye. Preferably, the composition contains Zincon and Ethyl violet, Zincon and Methyl violet, Zincon and Meldola's blue, Coomassie brilliant blue R and Phenosafranin, Coomassie brilliant blue G and Methyl orange, Calconcarboxylic acid and Rhodamine B, or Eriochrome black T and Rhodamine B. More preferably, the composition contains Zincon and Ethyl violet, Zincon and Methyl violet, Coomassie brilliant blue R and Phenosafranin, or Coomassie brilliant blue G and Methyl orange. Most preferably, the composition contains Zincon and Ethyl violet, or Zincon and Methyl violet. In the present composition, preferably, Zincon has a concentration of 0.001–0.02% by weight of the volume of the composition. Preferably, the molar ratio of Zincon to Methyl violet or Ethyl violet is 1 to 0.8 and the composition further contains 7 v/v % acetic acid-containing 35 v/v % aqueous methanol solution.

Another aspect of the present invention provides a counter-dye composition for detection of protein on polyacrylamide gels containing an acidic organic dye and a basic organic dye. Preferably, the composition contains Zincon and Ethyl violet, Zincon and Methyl violet, Zincon and Meldola's blue, Coomassie brilliant blue R and Phenosafranin, Coomassie brilliant blue G and Methyl orange, Calconcarboxylic acid and Rhodamine B, or Eriochrome black T and Rhodamine B. More preferably, the composition contains Zincon and Ethyl violet, Zincon and Methyl violet, Coomassie brilliant blue R and Phenosafranin, or Coomassie brilliant blue G and Methyl orange. Most preferably, the composition contains Zincon and Ethyl violet, or Zincon and Methyl violet. In the present composition, preferably, Zincon has a concentration of 0.001–0.02% by weight of the volume of the composition. Preferably, the molar ratio of Zincon to Methyl violet or Ethyl violet is 1 to 0.8 and the composition further contains 7 v/v % acetic acid-containing 35 v/v % aqueous methanol solution.

BEST MODE FOR CARRYING OUT THE INVENTION

Figure 1A:
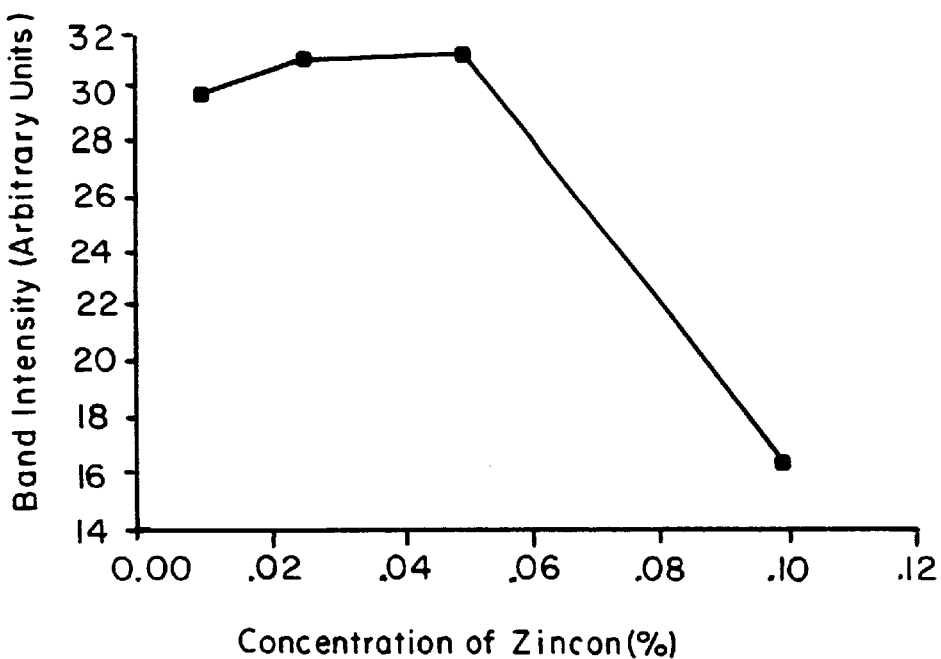
FIGS. 1a to 1c are graphs which show the intensity of the stained protein band according to a concentration of Zincon (a), Calconcarboxylic acid (b) and Eriochrome black T (c), respectively.

Hereinafter, the present invention will be more specifically explained.

To establish a novel staining method to solve the problems involved in the prior method and to give a higher sensitivity than the prior method, the present inventors have conceived a counter-dye staining method using a counter-dye composition containing two kinds of organic dyes, and repeated the extensive studies for appropriately matching the organic dyes. As a result, we have discovered surprisingly that by using an acidic organic dye in combination with a basic organic dye, staining and destaining procedure can be shortened and simplified, and furthermore, the sensitivity becomes 2–50 times higher than that of the prior CBBR or CBBG staining method.

In the present counter-dye staining method, an acidic organic dye is a main dye and a basic organic dye is an assistant dye having counter-ion effects. That is, the basic organic dye acts as a counter-ion to the acidic organic dye to form an ion-pair with the acidic organic dye, and thereby the acidic organic dye can be prevented from infiltrating into a gel background except for protein, so as to shorten or even omit destaining procedure and further to improve the detection sensitivity. Furthermore, by using the counter-dye composition according to the present invention, the acidic and basic organic dye can bind with protein respectively to lead to double-staining and also the organic dye, which has been bound with protein, may bind with its counter-dye owing to their affinity. As a result, protein can be deeply stained on polyacrylamide gels.

An acidic organic dye which can be used in the present invention includes Zincon (formula 1), Coomassie brilliant blue R (formula 2), Coomassie brilliant blue G (formula 3), Calconcarboxylic acid (formula 4), and Eriochrome black T (formula 5). A basic dye which can be used in the present invention includes Ethyl violet (formula 6), Methyl violet (formula 7), Meldola's blue (formula 8), Phenosafranin (formula 9), Methyl orange (formula 10) and Rhodamine B (formula 11).

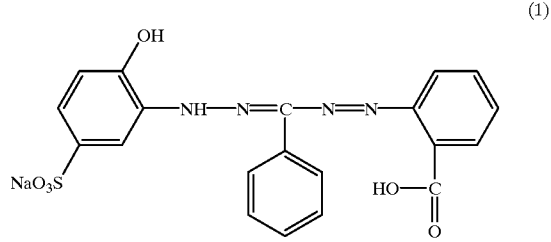

(1)

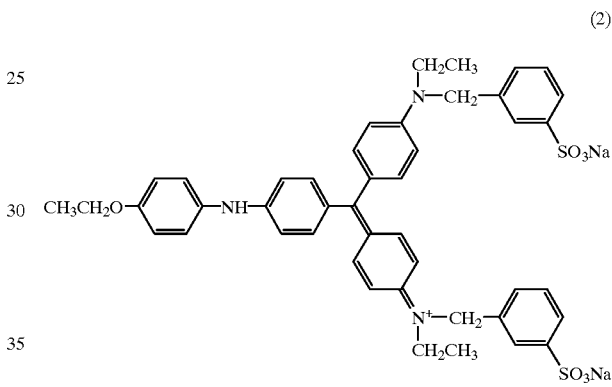

(2)

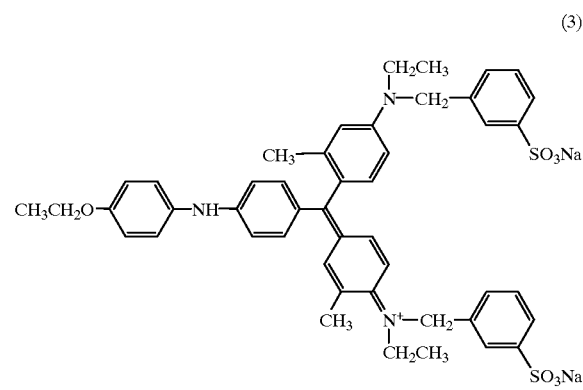

(3)

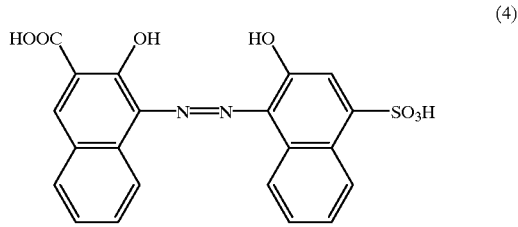

(4)

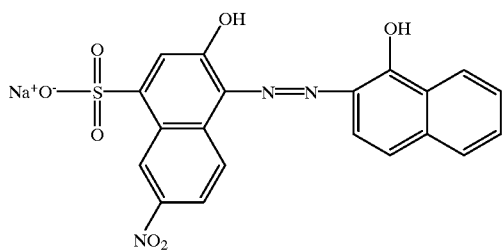

In the present invention, it is very important to appropriately match an acidic organic dye and a basic organic dye which have affinity each other In view of this, the counter-dye composition containing Zincon and Ethyl violet, the counter-dye composition containing Zincon and Methyl violet, the counter-dye composition containing Zincon and Meldola's blue, the counter-dye composition containing Coomassie brilliant blue R and Phenosafranin, the counter-dye composition containing Coomassie brilliant blue G and Methyl orange, the counter-dye composition containing Calconcarboxylic acid and Rhodamine B, or the counter-dye composition containing Eriochrome black T and Rhodamine B is preferable, and among the above compositions, the counter-dye composition containing Zincon and Ethyl violet, the counter-dye composition containing Zincon and Methyl violet, the counter-dye composition containing Coomassie brilliant blue R and Phenosafranin, or the counter-dye composition containing Coomassie brilliant blue G and Methyl orange is more preferable, and the counter-dye composition containing Zincon and Ethyl violet, or the counter-dye composition containing Zincon and Methyl violet is most preferable.

Dyes which can replace the above-described dyes in the present invention are listed in the following Table 1. All of these dyes lie within the scope of the present invention.

TABLE 1

| Counter-dye composition | Dye (C. I. number) | Replaceable dyes |
|---|---|---|
| Zincon + Ethyl violet | Zincon Ethyl violet (42600) | Eriochrome blue black R Methyl violet B base(42535B) Methyl violet 10B(42555) Methyl violet B(42535) Ethyl green |
| Zincon + Methyl violet | Zincon Methyl violet (42535) | Methyl violet B base(42535B) Methyl violet 10B(42555) Ethyl violet(42600) |
| Zincon + Meldola's blue | Zincon Meldola's blue | Crystal violet(42555) Victoria blue B(44045) Victoria blue R(44040) Victoria blue pure blue B0(42595) |
| Coomassie brilliant blue R + Phenosafranin | Coomassie brilliant blue R(42660) Phenosafranin | Coomassie brilliant blue R250 Coomassie brilliant blue R150 Coomassie brilliant blue R350 Variamine blue Crystal violet Methyl violet B Meldola's blue Bromothymol blue Victoria blue Methyl violet 2B |

TABLE 1-continued

| Counter-dye composition | Dye (C. I. number) | Replaceable dyes |
|---|---|---|
| Coomassie brilliant blue G + Methyl orange | Coomassie brilliant blue G(42665) Methyl orange | Methyl orange Acid violet 17 Variamine blue Crystal violet Methyl violet B Meldola's blue Bromothymol blue Victoria blue Methyl violet 2B Ethyl violet(42600) Phenosafranin |
| Calconcarboxylic acid + Rhodamine B | Calconcarboxylic acid Rhodamine B | Rhodamine B base(45170:1) Rhodamine B isothiocyanate Rhodamine 123 hydrate Rhodamine 6G(45160) |
| Eriochrome black T + Rhodamine B | Eriochrome black T Rhodamine B | Eriochrome blue black R Eriochrome blue black B Rhodamine B base(45170:1) Rhodamine B isothiocyanate Rhodamine 123 hydrate Rhodamine 6G(45160) |

Particularly, the counter-dye composition containing Zincon and Ethyl violet, or Zincon and Methyl violet is most preferable because it provides the improvement of the detection sensitivity as well as omission of destaining procedure. Therefore, the counter-dye composition containing Zincon and Ethyl violet or Methyl violet will be described in more detail hereinafter.

In the staining method using the counter-dye composition containing Zincon and Ethyl violet or Methyl violet, Ethyl violet or Methyl violet is added to Zincon at a relatively low concentration, which displays a similar color to that of protein band stained with Zincon, and they form precipitate to minimize the infiltration of Zincon into the gel background and to increase the intensity of protein band. Zincon as represented by the above chemical formula 1 is a O-hydroxyazo compound. Zincon is known as a metal chelating agent. Zincon forms a chelate compound with Zn, Cu or Hg, etc., under the alkaline condition at a pH of 8–10 (see [H. Flaschka and Huditz, J. Physiol. Chem, 289, 279 (1952)]). Since Zincon contains sulfonate, diazo and hydroxyl groups, it is classified as an acidic dye such as CBBR. Protein staining effects of Zincon are slightly changed according to pH and kind of solvent of solution. Zincon has excellent staining effects in the mixed solution of acetic acid-containing acidic methanol and water at a pH of about 2 (under the similar condition to that of CBBR staining method).

Ethyl violet of chemical formula 6 and Methyl violet of chemical formula 7, which are used in combination with Zincon, are classified as a triarylmethane basic dye. Ethyl violet is used in quantitation of lead or copper (see [Analyst (London), 112, 1011 (1987)]). Methyl violet is an acid-base indicator the color of which changes from yellow to green at a pH of 0.13–0.5, from green to blue at a pH of 1.0–1.5, and blue to violet at a pH of 2.0–3.0, respectively (see [J. of colloid and interface science, 164, 223–228 (1994)]). In the case of staining protein with Ethyl violet or Methyl violet alone in the same solution as with Zincon, the color of protein changes to blue and the sensitivity decreases slightly. In contrast, in the case of using Ethyl violet or Methyl violet in combination with Zincon, excellent synergistic staining effects can be obtained. That is, according to the present invention, Zincon is applied to staining protein on polyacrylamide gels in combination with Ethyl violet or methyl violet. As a result, the color of protein changes from red to violet, to make it possible to detect protein by direct visual inspection. Additionally, since the dyes bind rapidly with protein, detection procedure may be completed within 30–60 minutes without the subsequent destaining procedure. Moreover, in the case of using Zincon together with Ethyl violet or Methyl violet, the sensitivity is about 50 times higher than that of CBBR, whereas in the case of using Zincon alone, the sensitivity is nearly the same as that of CBBR.

In another aspect, in the case of using Rhodamine B, Phenosafranin or Methyl orange, direct visual sensitivity can be improved by the color contrast between background stained with Rhodamine B, Phenosafranin or Methyl orange, and blue-colored protein band.

The present counter-dye composition is prepared by mixing an acidic organic dye and a basic organic dye in acetic acid-containing acidic aqueous methanol solution as a solvent. Since the counter-dye composition according to the present invention produces a fine precipitate with the lapse of time after preparation due to the formation of an ion-pair between the acidic organic dye and the basic organic dye, it is preferably prepared immediately before its use.

Figure 1B:
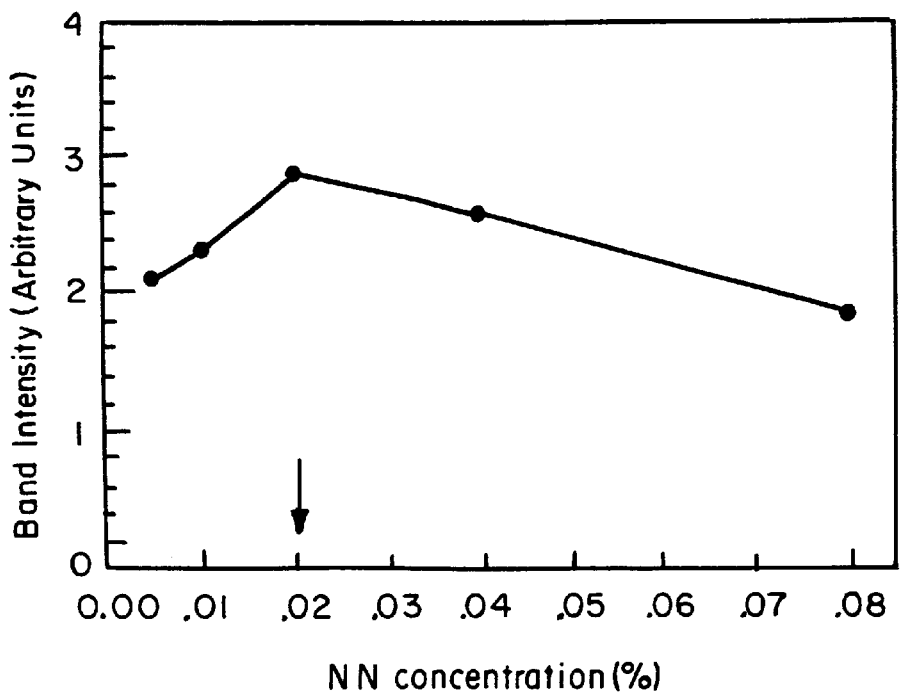
Figure 1C:
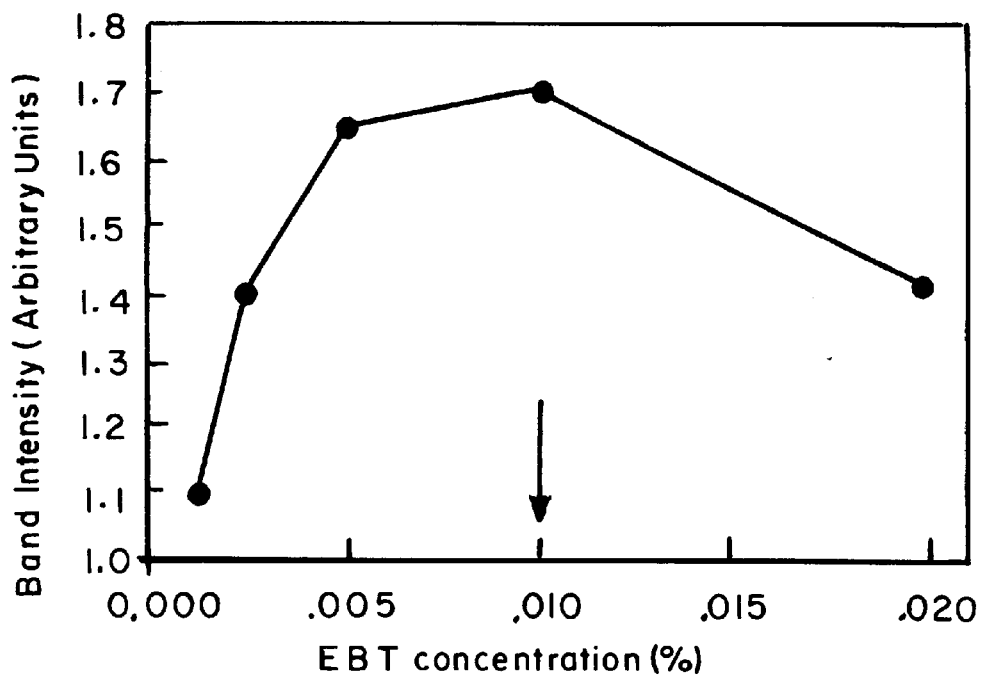

In the present invention, particle size of dye is very important and preferably, a fine precipitate is appropriately, i. e. not excessively, produced (see [Electrophoresis 6, 427–448 (1985)]). Representative factors having effects on the particle size are i) concentrations and mixing ratio of dyes, ii) the content ratio and kind of an alcohol as a solvent, and iii) a concentration of hydrogen ion. In view of the above factors, preferably, Zincon has a concentration of 0.001–0.02%, and most preferably, 0.004%, by weight of the volume of the composition. At a lower concentration than 0.001 w/v %, staining effects on protein band are not satisfactory and at a higher concentration than 0.02 w/v %, the difference in the intensities is decreased. This is apparent from FIG. 1a which shows the intensity of the stained protein band according to a concentration of Zincon. Other acidic dyes than Zincon, i. e. Calconcarboxylic acid (abbreviated to NN) and Eriocluome black T (abbreviated to EBT), show the similar pattern to Zincon with respect to the intensity of band according to a concentration of dye (FIGS. 1b and 1c). Mixing ratios of the acidic organic dye and the basic organic dye are changed with characteristics of the dyes. It is desirable to mix the dyes in the optimal ratio in which excessive precipitate is not formed and effects of the present invention are maximized (see Table 2). Particularly, in the case of using the counter-dye composition containing Zincon-Ethyl violet or Zincon-Methyl violet, it is preferable that 7 v/v % acetic acid-containing 35 v/v % aqueous methanol solution is used as a solvent and further, the molar ratio of Zincon to Ethyl violet or Methyl violet is 1 to 0.8. Under the above condition, since the infiltration of dyes into gel background can be minimized and binding of dyes with protein may not be interfered, particle size may be formed in which dyes can be most efficiently adsorbed to protein band.

The present invention is more specifically explained by the following examples. However, it should be understood that these examples are provided for more clear understanding of the constitution and effects of the present invention and are not intended to limit the scope of the present invention in any manners.

EXAMPLES 1 to 7

(1) Preparation of gels and electrophoresis

A SDS-containing slab gel was prepared according to Laemmli's method. A concentration of protein was determined by Bradford method using Bio-rad standard I for quantitation of protein (see [Anal. Biochem. 151, 369–374]). Before electrophoresis, 1.0, 0.5, 0.25, 0.1, 0.05, 0.025, 0.01, 0.005, 0.001 and 0.0005 $\mu$g of BSA were heated to 100° C. for 5 minutes in sample buffer solution (70 mM Tris-HCl, pH 6.8, 11.4% glycerol, 3% SDS, 0.01% bromophenol blue, $\beta$-mercaptoethanol) Developing buffer solution comprised 0.025M Tris, 0.2M glycine and 0.1% SDS and was at a pH of 8.3. The thickness of gel was 1 mm. Stacking gel (4.5%) having a length of 1.5 cm was stacked on separating gel (10%) (acrylamide:bisacrylamide=30:0.8). 1.0, 0.5, 0.25, 0.1, 0.05, 0.025, 0.01, 0.005, 0.001 and 0.0005 $\mu$g of BSA were loaded onto wells in order from the left. Then, electrophoresis was performed in Mini-protein II slab gel apparatus at 200V for 35 minutes.

(2) Staining and destaining

In order to elevate effects of a counter-dye composition and prevent gels from being stained with spots, the gels separated by electrophoresis were washed with agitation with 7 v/v % acetic acid-containing 20–40 v/v % aqueous methanol solution for 5–30 minutes. Since Zincon or Coomassie brilliant blue is sensitive, clean glassware were used and the gels were washed for 30 minutes.

According to the counter-dye composition, washing, staining and destaining time were adjusted as described in the following Table 2. The gels were washed with washing solution having the content ratio as described in the following Table 2 to remove interfering substances such as buffer, SDS, etc., and then, stained with agitation for 25–60 minutes with the counter-dye composition as described in the following Table 2. The counter-dye compositions were prepared by dissolving the acidic organic dye and the basic organic dye in 7 v/v % acetic acid-containing 20–40 v/v % aqueous methanol solution, immediately before their use. The residual dyes were removed from the stained gels in destaining solution (7 v/v % acetic acid-containing 20–40 v/v % aqueous methanol solution) for 5–30 minutes. In the case of using Zincon, the destaining procedure could be omitted owing to a light color of background and the gels were merely washed for 5 minutes to remove the residual dyes from the gels. The destained gels were dried at 60° C. for 30 minutes on Wattmann No. 1 filter paper. In the case of Zincon, the gel could be dried under the same condition as in the above, and stored for 1 week in the diluted counter-dye composition by 3 times. After destaining, concentrations of protein were measured on the gels by scanning at a maximum absorption wavelength of each of the stains using Shimadzu CS-9000 densitometer. The results are shown in the following Table 2.

TABLE 2

| Example | dyes | final conc. (optimal conc.) (w/v %) | time(min) washing | time(min) staining | time(min) destaining | the content ratio of washing, staining & destaining solution (v/v %) acetic acid/methanol/water | sensitivity (ng) |
|---|---|---|---|---|---|---|---|
| 1 | Zincon | 0.001–0.02 (0.004) | 30 | 30 | 5 | 7/35/58 | 1 |
|   | Ethyl violet | 0.001–0.02 (0.003) | | | | | |
| 2 | Zincon | 0.001–0.02 (0.004) | 30 | 30 | 5 | 7/35/58 | 1 |
|   | Methyl violet | 0.001–0.02 (0.0025) | | | | | |
| 3 | Zincon | 0.001–0.05 (0.0025) | 30 | 30 | 5 | 7/40/53 | 25 |
|   | Meldola's blue | 0.001–0.02 (0.005) | | | | | |
| 4 | CBBR | 0.001–0.05 (0.005) | 30 | 60 | 5 | 7/40/53 | 1 |
|   | Phenosafranin | 0.001–0.02 (0.0015) | | | | | |
| 5 | CBBG | 0.001–0.05 (0.005) | 30 | 30 | 5 | 7/20/73 | 1 |
|   | Methyl orange | 0.001–0.02 (0.002) | | | | | |
| 6 | Calconcarboxylic acid | 0.001–0.05 (0.02) | — | 25 | 30 | 7/40/53 | 25 |
|   | Rhodamine B | 0.001–0.1 (0.04) | | | | | |
| 7 | Eriochrome black T | 0.001–0.05 (0.01) | 5 | 25 | 30 | 7/40/53 | 10 |
|   | Rhodamine B | 0.001–0.05 (0.01) | | | | | |

TABLE 2-continued

| Example dyes | final conc. (optimal conc.) (w/v %) | time(min) wash-ing | time(min) stain-ing | time(min) dest-ain-ing | the content ratio of washing, staining & destaining solution (v/v %) acetic acid/methanol/water | sen-siti-vity (ng) |
|---|---|---|---|---|---|---|

*CBBR: Coomassie brilliant blue R, CBBG: Coomassie brilliant blue G

In Examples 1–7, most of protein bands have appeared within 30 minutes and background was clear without infiltration of dye. After 30 minutes, precipitate of dye complex was adsorbed more to protein band to display deep violet band and the sensitivity was increased to visualize even 1 ng of protein after 1–2 or 24 hours.

EXAMPLES 8 to 14

The procedures were carried out in the substantially same manner as in Examples 1–7, except that standard protein, which was prepared by mixing the equal amount of myosin (205 kDa), β-galactosidase (116 kDa), phosphoiylase b (97.4 kDa), BSA (66 kDa), ovalbumin (45 kDa) and carbonic anhydrase (29 kDa) was loaded respectively at a concentration of 10,000, 5,000, 2,500, 1,250, 625, 313, 156, 78, 39, and 19 ng onto the wells in order from the left. The results are shown in FIGS. 3a to 3g.

EXAMPLES 15 to 18

The procedures were carried out under nondenaturing condition using standard protein, which was prepared by mixing the equal amount of BSA (66 kDa), ovalbumin (45 kDa), carbonic anhydrase (29 kDa) and trypsin inhibitor (29 kDa) was loaded respectively at a concentration of 1,000, 300, 100, 30, and 10 ng onto the wells of non-SDS polyacrylamide gels in order from the left. The results are shown in FIGS. 4a to 4d.

COMPARATIVE EXAMPLE 1

Figure 2A:
FIGS. 2a to 2h are photographs which show the detection sensitivity of BSA protein on a SDS-polyacrylamide gel stained with Zincon-Ethyl violet (a), Zincon-Methyl violet (b), Zincon-Meldola's blue (c), Coomassie brilliant blue R-Phenosafranin (d), Coomassie brilliant blue G-Methyl orange (e), Calconcarboxylic acid-Rhodamine B (f), Eriochrome black T-Rhodamine B (g) and CBBR (h), respectively.
Figure 2B:
Figure 2C:
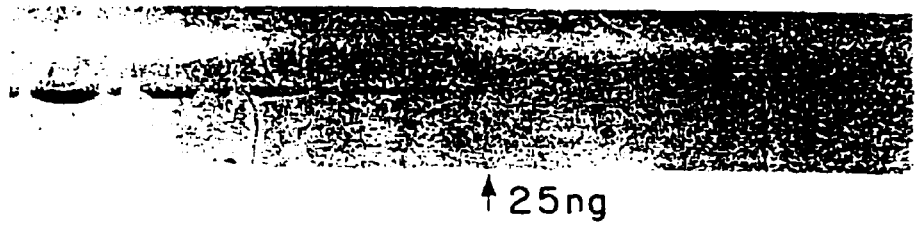
Figure 2D:
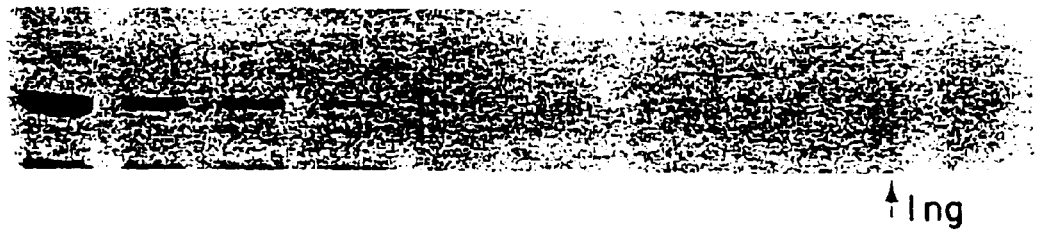
Figure 2E:
Figure 2F:
Figure 2G:
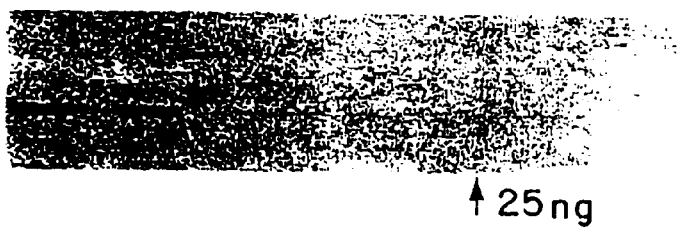
Figure 2H:
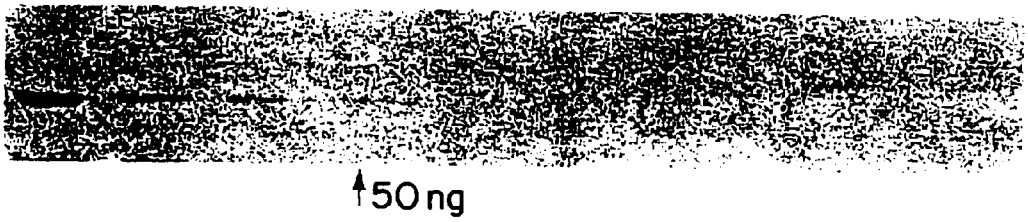

The procedures were carried out in the substantially same manner as in Examples 1 to 7, except that using 0.2% solution of CBBR-250 as a dye and 7 v/v % acetic acid-containing 40 v/v % aqueous methanol solution as a solvent, staining was performed for 1 hour and then, destaining was performed for 2 hours. The result is shown in FIG. 2h.

COMPARATIVE EXAMPLE 2

Figure 3A:
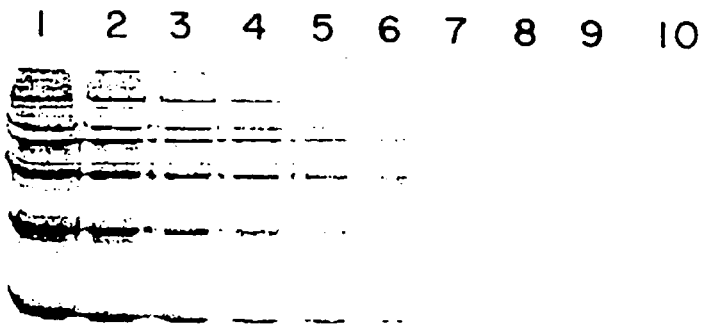
FIGS. 3a to 3h are photographs which show the detection sensitivity and staining pattern of standard protein on a SDS-polyacrylamide gel stained with Zincon-Ethyl violet (a), Zincon-Methyl violet (b), Zincon-Meldola's blue (c), Coomassie brilliant blue R-Phenosafranin (d), Coomassie brilliant blue G-Methyl orange (e), Calconcarboxylic acid-Rhodamine B (f), Eriochrome black T-Rhodamine B (g) and CBBR (h), respectively.
Figure 3B:
Figure 3C:
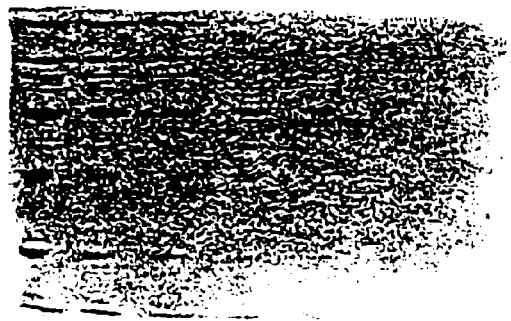
Figure 3D:
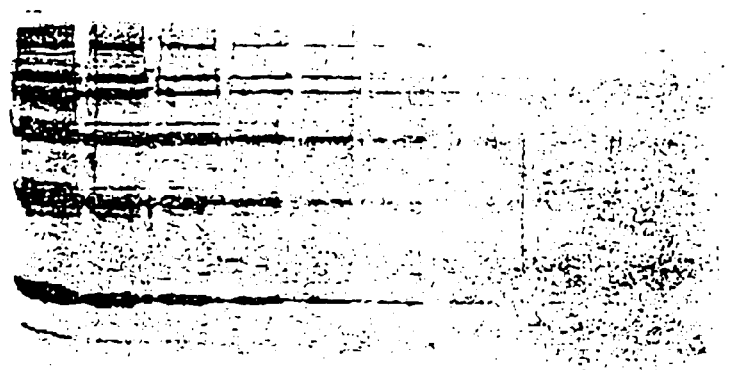
Figure 3E:
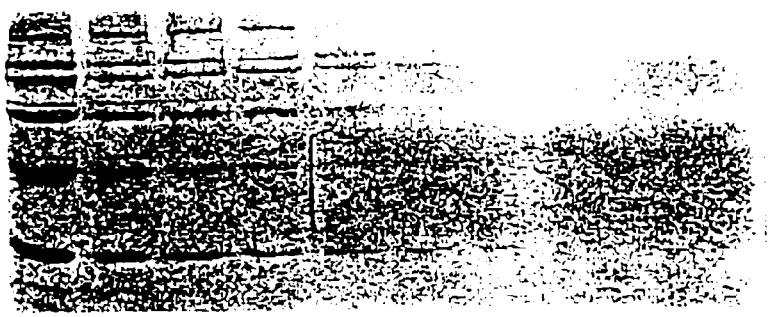
Figure 3F:
Figure 3G:
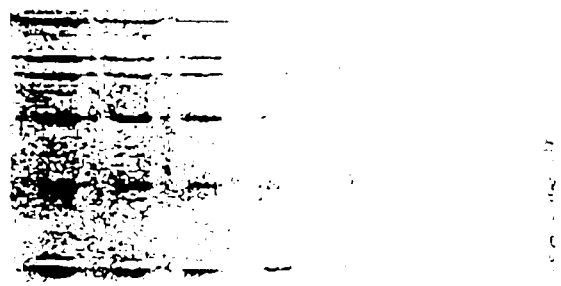
Figure 3H:
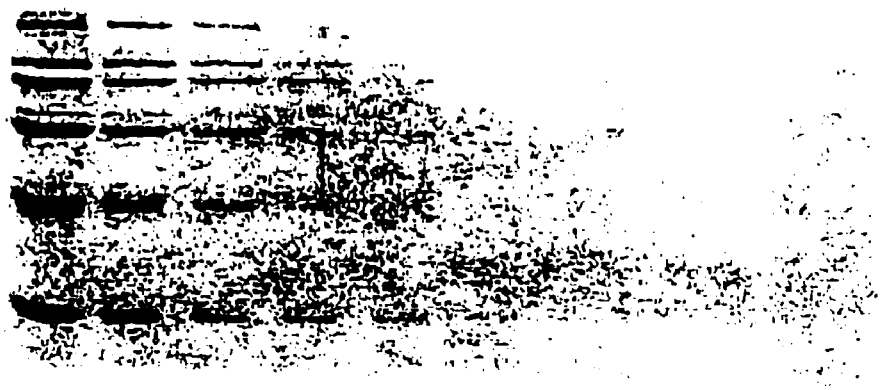

The procedures were carried out in the substantially same manner as in Examples 8 to 14, except that using 0.2% solution of CBBR-250 as a dye and 7 v/v % acetic acid-containing 40 v/v % aqueous methanol solution as a solvent, staining was performed for 1 hour and then, destaining was performed for 2 hours. The result is shown in FIG. 3h.

COMPARATIVE EXAMPLE 3

Figure 4A:
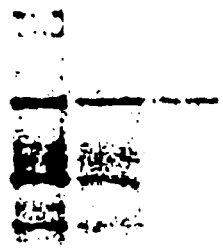
FIGS. 4a to 4e are photographs which show the detection sensitivity and staining pattern of standard protein on a non-SDS-polyacrylamide gel stained with Zincon-Ethyl violet (a), Zincon-Methyl violet (b), Coomassie brilliant blue R-Phenosafranin (c), Coomassie brilliant blue G-Methyl orange (d) and CBBR (e), respectively.
Figure 4B:
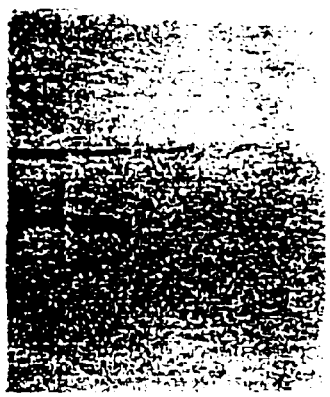
Figure 4D:
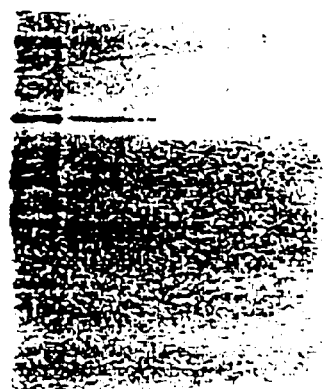
Figure 4C:
Figure 4E:
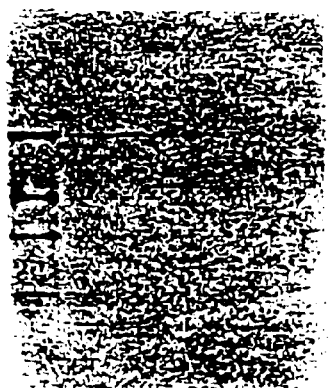

The procedures were carried out in the substantially same manner as in Examples 15 to 18, except that using 0.2% solution of CBBR-250 as a dye and 7 v/v % acetic acid-containing 40 v/v % aqueous methanol solution as a solvent, staining was performed for 1 hour and then, destaining was performed for 2 hours. The result is shown in FIG. 4e.

From FIGS. 2a to 2h, since 1–25 ng of BSA was visualized in the counter-dye staining method according to the present invention, whereas 50 ng of BSA was visualized in the prior CBBR staining method, it can be seen that the present method increases the detection sensitivity by 2–50 times. From FIGS. 3a to 3h, it can be seen that the detection sensitivity of the present method is 2–50 times higher than that of the prior CBBR method, although staining pattern is identical each other. Additionally, from FIGS. 4a to 4e, it can be seen that the sensitivity of the present method is 3–10 times higher than that of the prior CBBR method on non-SDS polyacrylamide gels.

According to the counter-dye staining method of the present invention, an acidic organic dye is used in combination with a basic organic dye which forms an ion-pair with the acidic organic dye. As a result, the present method has the following effects: i) to minimize staining of gel background, ii) to have synergistic staining effect by the basic organic dye, iii) shorten the detection time within 1 hour, and iv) increase the detection sensitivity by 2–50 times.

Therefore, the present invention provides a method for detection of protein in a 2–50 times higher sensitivity than that of the prior CBBR or CBBG method on SDS or non-SDS polyacrylamide gels in a rapid and simple manner, by staining the polyacrylamide gels with a counter-dye composition containing an acidic organic dye and a basic organic dye and the counter-dye composition for detection of protein on SDS or non-SDS polyacrylamide gels.

What is claimed is:

1. A method for the detection of protein on polyacrylamide gels comprising the steps of staining the polyacrylamide gels with a counter-dye composition containing an acidic organic dye and a basic organic dye, wherein the acidic organic dye and the basic organic dye are selected from the group consisting of Zincon and Ethy violet, Zincon and Methyl violet, Zincon and Meldola's blue, Coomassie brilliant blueR and Phenosafranin, Coomassie brilliant blue G and Methyl orange, Calconcarboxylic acid and Rhodamine B, and Eriochrome black T and Rhodamine B and protein complexes with the counter-dye composition, and observing protein-counter-dye complexes.

2. The method according to claim 1, wherein the counter-dye composition contains dyes selected from the group consisting of Zincon and Ethyl violet, Zincon and Methyl violet, Coomassie brilliant blue R and Phenosafranin, and Coomassie brilliant blue G and Methyl orange.

3. The method according to claim 2, wherein the counter-dye composition contains Zincon and Ethyl violet, or Zincon and Methyl violet.

4. The method according to claim 3, wherein Zincon has a concentration of 0.001–0.02% by weight of the volume of the composition.

5. The method according to claim 3, wherein the molar ratio of Zincon to Ethyl violet or Methyl violet is 1 to 0.8.

6. The method according to claim 3, wherein the counter-dye composition further contains 7 v/v % acetic acid-containing 35 v/v % aqueous methanol solution.

* * * * *